(12) United States Patent
Garibaldi et al.

(10) Patent No.: US 6,522,909 B1
(45) Date of Patent: Feb. 18, 2003

(54) METHOD AND APPARATUS FOR MAGNETICALLY CONTROLLING CATHETERS IN BODY LUMENS AND CAVITIES

(75) Inventors: Jeffrey M. Garibaldi, St. Louis, MO (US); Rogers C. Ritter, Charlottsville, VA (US); Gerard H. Epplin, St. Louis, MO (US); Walter M. Blume, Webster Groves, MO (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/370,067

(22) Filed: Aug. 6, 1999

Related U.S. Application Data
(60) Provisional application No. 60/095,710, filed on Aug. 7, 1998.

(51) Int. Cl.$^7$ ................................................ A61B 5/05
(52) U.S. Cl. ........................ 600/424; 600/117; 600/407; 128/899; 324/207.11
(58) Field of Search ................................ 600/424, 407, 600/425, 117; 324/207.11, 200, 207.22; 128/899

(56) References Cited

U.S. PATENT DOCUMENTS

| | | | |
|---|---|---|---|
| 4,054,128 A | * | 10/1977 | Seufert |
| RE34,663 E | * | 7/1994 | Seale |
| 6,014,580 A | * | 1/2000 | Blume et al. |

\* cited by examiner

Primary Examiner—Marvin M. Lateef
Assistant Examiner—Runa Shah Qaderi

(74) Attorney, Agent, or Firm—Harness, Dickey & Pierce, P.L.C.

(57) ABSTRACT

A method of navigating a magnet-tipped distal end of an elongate medical device through the body includes providing an image display of the part of the body through which the medical device is being navigated and using the display to input the desired path of the medical device by identifying points on the desired path on the display. The magnetic field needed to orient the end of the medical device in the direction of the desired path as indicated on the display is then determined. In one embodiment where only points on the desired path are identified, the field direction is the direction indicated by the points on the desired path. In a second embodiment, where points on the current path and the desired path are identified, the desired angle of deflection is determined, and the direction of the magnetic field is set to lead this desired angle of deflection by 90° to over torque the end of the catheter, and the intensity of the field is determined from a table of experimentally determined field intensities for given angles of deflection.

The apparatus for navigating a magnet-tipped medical device through the body in accordance with the invention includes a magnet system for applying a magnetic field to the magnet-tipped distal end of the medical device to orient the distal end of the medical device; a computer for controlling the magnet system to generate a specified magnetic field in the body part; first and second imaging devices connected to the computer, for providing bi-planar images of the body part through which the medical device is being navigated; first and second displays for displaying the images from the image devices; and an input device for inputting points identifying the desired path of the medical device on each of the displays. The computer is programmed to determine the magnetic field necessary to control orient the medical device on the path input on the displays.

2 Claims, 5 Drawing Sheets

METHOD AND APPARATUS FOR MAGNETICALLY CONTROLLING CATHETERS IN BODY LUMENS AND CAVITIES

This is a continuation of copending provisional application Serial No. 60/095,710; filed on Aug. 7, 1998.

FIELD OF THE INVENTION

This invention relates to magnetically controlling catheters, and in particular to a method and apparatus for magnetically controlling catheters in body lumens and cavities.

BACKGROUND OF THE INVENTION

It has long been proposed to navigate a magnet-tipped catheter through the body with an externally applied magnetic field. See for example Yodh, A New Magnet System for Intravascular Navigation, Medical and Biological Engineering, Vol. 6, No. 2, March 1968. However, until this invention, the methods of navigating have been too crude and unreliable for serious medical applications. Thus, at the present time the guidance of catheters and other medical devices in body lumens and cavities is still most often accomplished by providing a bent tip on the device or using a guide wire with a bent tip. The physician applies torque and axial push force on the proximal end of the medical device or guidewire to effect tip direction and axial advancement at the distal end. This method of orienting and advancing the tip has several limitations. First, the torque and axial push force is randomly distributed to the distal tip due to the length of the catheter and the tortuousness of the path. Second, the alignment of the catheter in the required direction needs to be synchronized with the advancement of the catheter without changing the catheter orientation. With these two complications, it becomes very difficult to control the distal tip of the catheter from the proximal end. Another method of navigating medical devices through the body is to use blood flow in blood vessels to guide the device through the blood vessels. Although these navigation techniques are effective, they are tedious, require extraordinary skill, and result in long medical procedures that fatigue the user.

SUMMARY OF THE INVENTION

The method and apparatus of the present invention facilitate the navigation of a magnet-tipped medical device through body lumens and cavities. Generally, the method of the present invention comprises: inputting information about the desired path of the medical device; determining the appropriate magnetic field direction and intensity to orient the distal end of the medical device in the direction of the desired path, and applying a magnetic field to the distal end of the medical device to orient the distal end in the direction of desired path. In accordance with this invention, path information is input by providing bi-planar displays of the portion of the body through which the medical device is being navigated. The desired path, and more particularly points along the desired path, is identified on each of the displays. In accordance with a first embodiment of this invention, the user identifies the point where the user desires a direction change (which is usually where the catheter tip is positioned) and a point on the desired new path on each of the displays. The identification of the points on the two bi-planar displays uniquely identifies the points in the three dimensional space inside the body part. The direction of the line or vector including the two points is then determined, and the magnet system is operated to create a magnetic field in the direction of this vector, to orient the distal tip of the catheter.

In accordance with a second embodiment of this invention, the user identifies three points on the two bi-planar displays: a point on the current path of the catheter, the point where the user desires to initiate a direction change, and a point on the desired new path of the catheter. The identification of the points on the two bi-planar displays uniquely identifies the points in the three dimensional space inside the body part. The desired angle of deflection is then determined, and the magnet system is controlled to apply a magnetic field in a direction that provides the maximum over torque (i.e., leads the desired angle of deflection by 90° in the same plane as the desired angle of deflection). The intensity of the magnetic field is determined based upon a table of empirical data which characterizes the required magnetic field strength for a given angle of deflection for a particular medical device.

Generally, the apparatus of the present invention comprises a magnet system for applying a magnetic field to the magnet-tipped distal end of a medical device, to navigate, orient, and hold the distal end of the medical device in the body. The apparatus also includes a computer for controlling the magnet system. First and second imaging devices, connected to the computer, provide images of the body part through which the catheter is being navigated. The computer displays these images on two displays. A controller, connected to the computer, has a joystick and trigger for the user to input points on the displays for two-point and three-point navigation according to the principles of the present invention.

The method and apparatus of the present invention are particularly adapted for use with an elongated medical device such as a catheter, but could be used with a guidewire or other device. In the preferred embodiment, the catheter consists of a distal section that contains a permanent or permeable magnet with an inner hole to allow the passage of fluids and other agents.

The method and apparatus of this invention allow for fast and efficient navigation of magnetic tipped catheters and other medical devices in the body. The method and apparatus provide an easy to use, intuitive interface that allows the user to identify the desired path on an image of the body. The angle of change and the necessary magnetic field to effect that change are automatically determined. The determination of the necessary magnetic field automatically accounts for the lag angle and other physical properties of the catheter. A limit on the angle of deflection can also be imposed to reduce the time necessary for the magnet system to operate, thereby speeding the navigation through the body. These and other features and advantages will be in part apparent, and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figure 1:
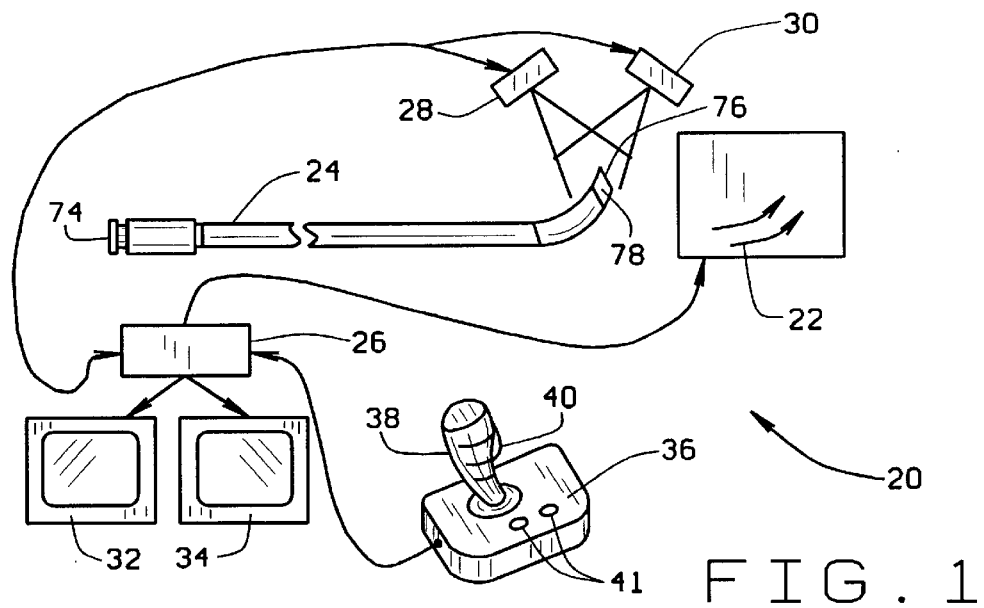
FIG. 1 is a schematic view of an apparatus for navigating a catheter through body lumens and cavities in accordance with the principles of this invention.

An apparatus for navigating a medical device through body lumens and cavities constructed in accordance with the principles of this invention is indicated generally as 20 in FIG. 1. The apparatus 20 includes a magnet system 22 for applying a magnetic field to the magnet-tipped distal end of a medical device such as catheter 24, to navigate the distal end of the catheter through a portion of the body. While the description of the preferred embodiment references catheter 24, it is understood that method and apparatus apply to other medical devices having magnetically steerable distal ends, e.g., guidewires, endoscopes, etc. The apparatus 20 also includes a computer 26 for controlling the magnet system 22. First and second imaging devices 28 and 30, connected to the computer 26, provide bi-planar images of the body part through which the catheter 24 is being navigated. The computer 26 displays these images on displays 32 and 34. The computer 26 also displays interface information on the displays to facilitate inputting information about the desired path. A controller 36, connected to the computer 26, has a joystick 38 and trigger or button 40 for the user to operate the apparatus 20. The magnet system 22 is preferably a set of electromagnetic coils that can be disposed around the body part to create a magnetic field within the body part of variable direction and intensity. A suitable magnet system 22 is that disclosed in U.S. Pat. No. 4,869,247, issued Sep. 26, 1989, entitled Video Tumor Fighting System and U.S. Pat. No. 5,125,888, issued on Jun. 30, 1992, entitled Magnetic Stereotactic System for Treatment Delivery, the disclosures of which are incorporated herein by reference.

The computer 26 preferably includes an image processing module programmed to input the x-ray images from the imaging devices 28 and 30, and overlaying the text of the system's status and displaying the current position of the joystick controller 36 (i.e., the cursor). The computer 26 provides standard capabilities that would be utilized in a typical x-ray imaging suite. Those features include bi-planar fluoroscope, background images, roadmaps, fluoroscope over roadmaps, roadmap acquisition review, image storing, in addition to other features. To direct the catheter 24, the user first enables the fluoroscope mode to position the catheter. A bi-planar background image is then captured. While injecting x-ray opaque contrast dye, a bi-planar roadmap image is stored. Using the joystick 38, the physician indicates the direction to orient the catheter. This is accomplished by selecting several points on each of the x-ray images. A wide variety of suitable computer systems and image processors are available. The inventors have implemented the apparatus with a Motorola VME processor, a Datacube MV-200 Image Processing Module, and a Matrix Daadio Multi-function I/O Module.

Figure 4:
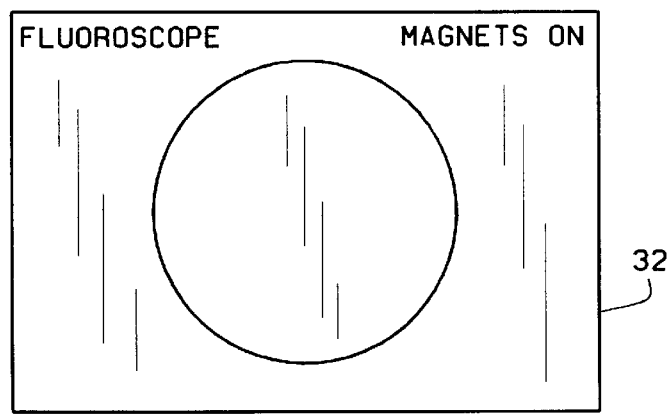
FIG. 4 is a front elevation view of a possible layout of one of the displays employed in the apparatus of the present invention.

The imaging devices 28 and 30 are preferably x-ray fluoroscopes that provide real-time images of the body part through which the catheter 24 is being navigated. The imaging devices 28 and 30 are arranged so that each provides an image of the same portion of the body part, but at different orientations or planes. The imaging devices 28 and 30 are preferably oriented at right angles to each other so that their respective images are in perpendicular planes, but this is not essential. When perpendicular, the imaging device 28 provides a view in the X-Z plane and the imaging device 30 provides a view in the Y-Z plane. The imaging devices 28 and 30 are connected to the computer 26, which processes the image signals and displays the processed images on displays 32 and 34. The displays 32 and 34 show the internal structure of the body part through which the catheter 24 is being navigated, as well as the present location of the catheter in the body part. As shown in FIG. 4, the images are displayed on the screen of the displays 32 and 34. The displays 32 and 34 can also provide other status information about the system 20, for example, the status of the magnet system 22. In the preferred embodiment, there are two separate displays 32 and 34, each on a separate display device. However, it should be understood that both displays 32 and 34 could be displayed juxtaposed on a single display device, or the displays 32 and 34 could be displayed alternately on a single display device.

Although in the preferred embodiment two imaging devices are used, other imaging techniques, for example CT or MRI imaging can be used, which can provide a three dimensional image of the body part with just one imaging device. In such a case, a single imaging device may be used instead of two imaging devices. Furthermore, while in the preferred embodiment two displays 32 and 34 are used, it may be possible through image processing or through the use of three-dimensional imaging techniques such as CT or MRI imaging, to show the body part in three dimensions in a single display. In this case, the desired catheter path or points on the desired catheter path can be identified on the single display without departing from the principles of this invention.

The computer 26 also provides an interface for the user to control the magnet system 22 through the displays 32 and 34. The user identifies the desired path for the catheter 24 on each of the displays 32 and 34. This is conveniently done with the joystick controller 36, which can manipulate markers that the computer 26 overlays on the displays 32 and 34 to identify points on the desired path of the catheter 24 for providing input information to the computer 26 for controlling the magnet system 22.

According to a first embodiment of this invention, the user identifies the desired path of the distal tip of the catheter 24 on each the displays 32 and 34 by identifying a point on the display where the user desires to change the direction of the catheter (typically where the catheter tip is positioned) and a point on the desired new path of the distal tip of the catheter. From the identification of these points, the desired three dimensional orientation of the distal end of the catheter is determined. Once the desired orientation is determined, the magnet system 22 applies a magnetic field of the orientation and strength-specified. According to a second embodiment of this invention, the user identifies the current path and the desired path of the distal tip of the catheter on each of the displays by identifying a point on the current path of the distal tip of the catheter, a point where the user desires to change the direction of the catheter, and a point on the desired new path of the distal tip of the catheter. From the identification of these points, the desired angle of deflection is determined. Once the desired angle of deflection is determined, the appropriate orientation and field intensity of the magnetic field are determined. In the second preferred embodiment, the orientation of the magnetic field leads the desired angle of deflection by 90° so that the magnetic field applies a maximum over torque to the distal tip of the catheter. The intensity of the magnetic field is determined from an empirically determined table of field intensities required to achieve a desired deflection angle, for the particular catheter 24.

The output of the x-ray/fluoroscopes 28 and 30 are connected to the computer 26 with an image processing module. The image processing module is programmed to input the x-ray images, apply overlay text of the system status, and to indicate the current position of the joystick controller (the cursor). The user uses the joystick 38 of the joystick controller 36 to select positions on the x-ray images on the displays 32 and 34 to indicate the desired orientation of the catheter 24. After selecting the orientation of the catheter, a button is pressed on the joystick controller 36 to initiate computer control of the magnet system 22. The computer 26 computes the required external magnetic field strength and/or direction to orient the catheter 24 as indicated on the displays 32 and 34. From this calculation, the computer 26 determines the power settings of each of the magnet coils within the magnet system 22. The computer 26 then programs digital-to-analog output modules to the determined settings to control each of the magnet power supplies in the magnet system 22. The composite field generated by each of the magnets within the magnet system 22 is equivalent to the predetermined field direction and strength for the current catheter tip location.

The computer 26 provides a convenient user interface to facilitate the input of orientation information via the displays 32 and 34. More specifically, in the two point navigation system of the first preferred embodiment of the present invention, the user identifies the point where the user desires to change the direction of the catheter by manipulating a marker over this point on one of the displays with the joystick 38 of controller 36, and locking the marker in place by pressing one of the buttons 40 on the joystick controller. The user then identifies a point on the desired new path of the catheter 24 in the same manner, using the joystick 38 of controller 36 to manipulate a marker over this point on the display, and locking the marker in place by pressing one of the buttons 40 on the joystick controller. After these two points have been identified on the display, the user then switches to the other display and identifies the two points on the other display in the same manner, using the joystick 38 of the joystick controller 36 to manipulate markers over the points, and locking the markers in place by pressing one of the buttons 40 on the joystick controller. Indicia appear on the second display to indicate the line along which the points identified on the first display lie, to facilitate the identification of the points on the second display.

Additional controls can be provided, for example buttons 41 on controller 36, to refine the direction control of the medical device. For example, in the two-point navigation system of the first preferred embodiment, the buttons 41 could increase and decrease the field strength. Increasing the field strength causes the distal end of the catheter to more closely conform to the magnetic field direction, decreasing the lag angle, and decreasing the field strength increases the lag angle. In the three-point navigation system, the buttons 41 could increase or decrease the field strength and/or change the direction of the magnetic field, to increase and decrease the angle of deflection. These controls allow fine adjustment of the catheter orientation without the need to reposition the catheter tip using the two-point or three-point navigation system.

Figure 5A:
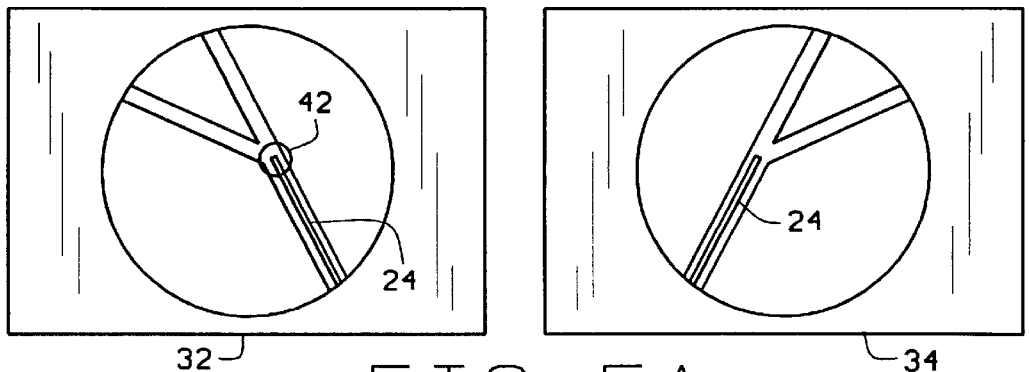
FIGS. 5A–5D are front elevation views of the two displays employed in the apparatus of the present invention, showing the steps for inputting points for the two-point navigation system of the first preferred embodiment.
Figure 5B:
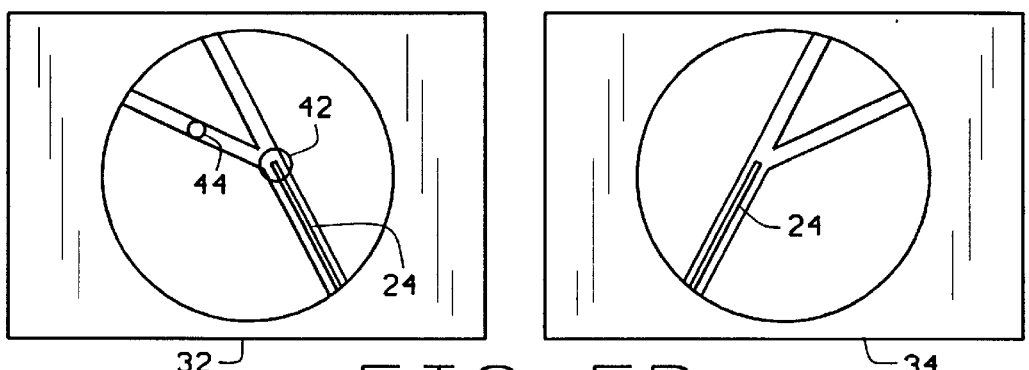
Figure 5C:
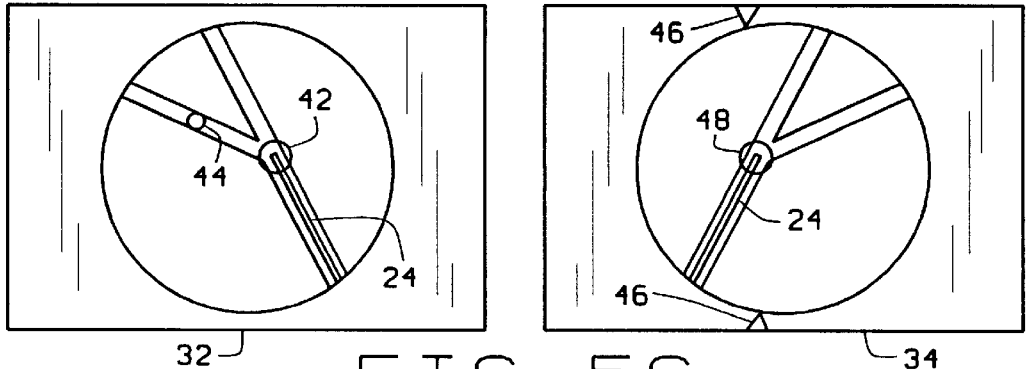
Figure 5D:
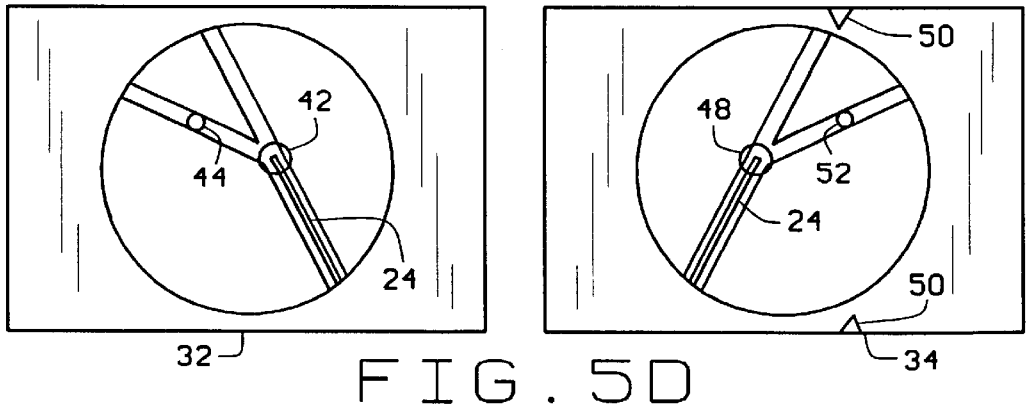

The identification process in the two-point navigation system of the first preferred embodiment is shown in FIGS. 5A–5D. In FIG. 5A, the user uses joystick 38 on the joystick controller 36 to manipulate marker 42 on display 32 over the point where the user wants to change the direction of the catheter and presses button 40 to lock the marker in place. In FIG. 5B, the user then uses the joystick 38 on the joystick controller 36 to manipulate marker 44 on the display 32 over a point on the desired new path of the catheter, and presses button 40 to lock the marker in place. Once these two points have been identified, the user switches to display 34. In the preferred embodiment this is done by using the joystick 38 to manipulate a cursor on the display 32 to the display, adjacent to display 34, to cause the cursor to switch to the display 34. As shown in FIG. 5C, indicators 46 appear at the top and bottom of the display 34 to indicate the line along which the marker 42 on display 32 lies, to help the user identify the same point on display 34. The user then uses the joystick 38 on the joystick controller 36 to manipulate marker 48 over the corresponding point on display 34 where the user wants to change the direction of the catheter. When the marker 48 is properly positioned, the user locks the marker in position by pressing a button 40 on the joystick controller 36. As shown in FIG. 5D, indicators 50 then appear at the top and bottom of the display to indicate the line along which marker 44 on screen 32 lies, to help the user identify the same point on display 34. The user uses the joystick 38 on the joystick controller 36 to position marker 52 on a point on the desired new path of the catheter, and locks the marker by pressing a button 40 on the joystick controller.

The markers 42 and 48 on screens 32 and 34, respectively, identify the point where the user desires to change the direction of the catheter, and preferably have similar size and shape to indicate to the user that they identify the same point. In the first preferred embodiment markers 42 and 48 are medium circles, but could, of course, have some other size, shape, and appearance. Similarly, the markers 44 and 52 on screens 32 and 34, respectively, identify a point on the desired new path of the catheter, and preferably have similar sizes and shapes to indicate to the user that they identify the same point. In the first preferred embodiment markers 44 and 52 are small circles, but could, of course, have some other size, shape, and appearance.

The markers 42 and 48 and 44 and 52 identify unique points in three dimensional space in the body part. The computer 26 determines the direction of the line between these two points, and cause the magnet system 22 to generate a magnetic field in the same direction, which causes the magnet on the distal end of the catheter 24 to align the distal end of the catheter in the same direction. The intensity of the magnetic field is preset or selected by the user balancing the need for magnetic field strength versus the need for efficiency.

Figure 6A:
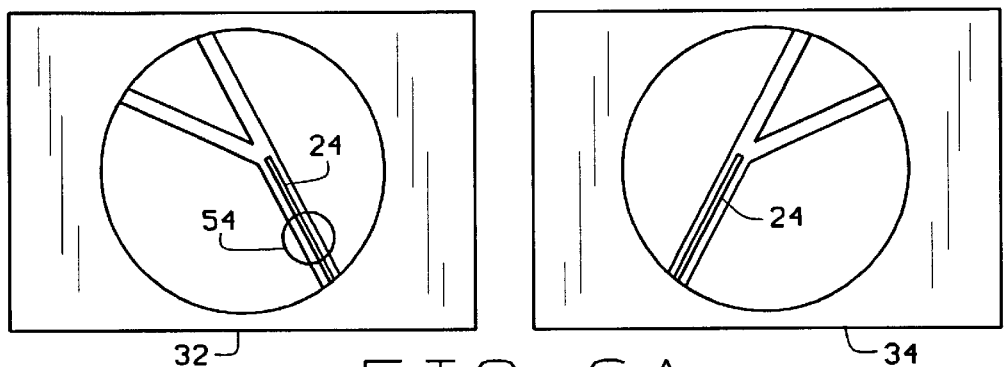
FIGS. 6A–6F are front elevation views of the two displays employed in the apparatus of the present invention, showing the steps for inputting points for the three-point navigation system of the second preferred embodiment.
Figure 6B:
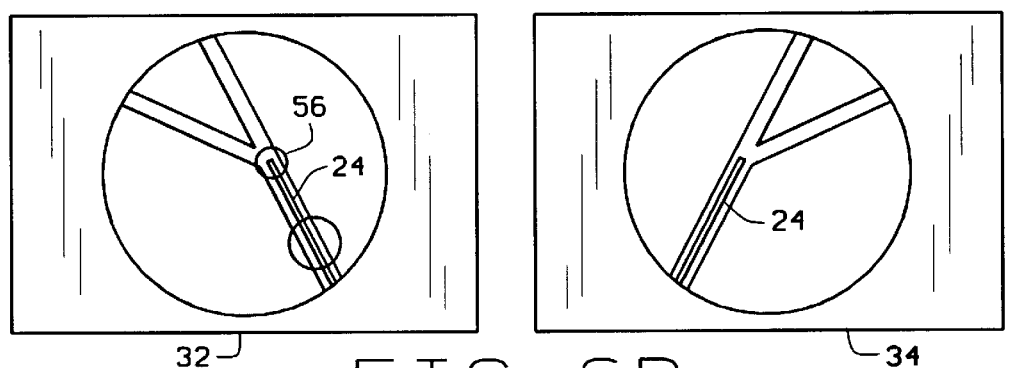
Figure 6C:
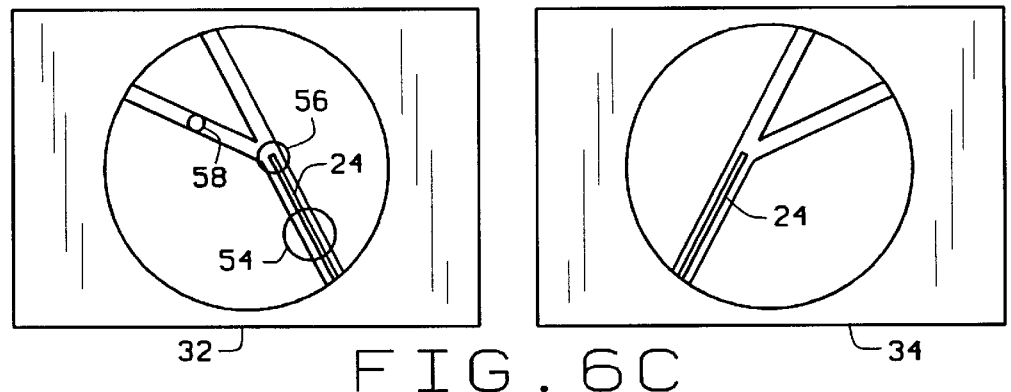
Figure 6D:
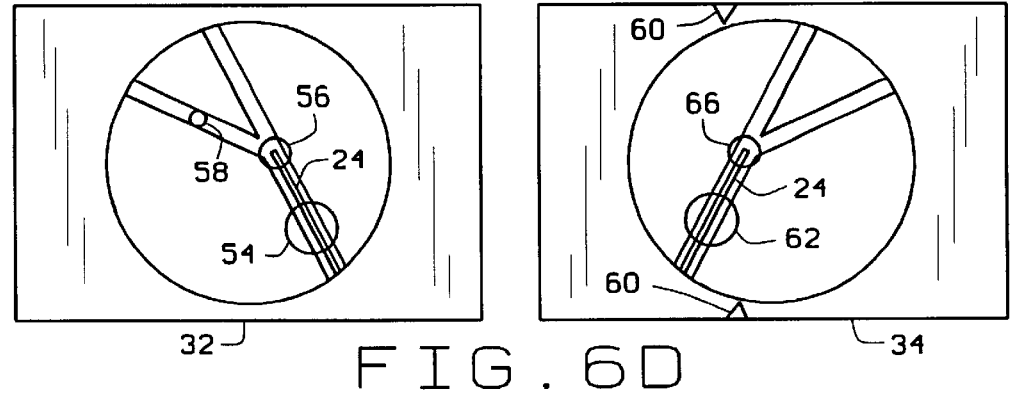
Figure 6E:
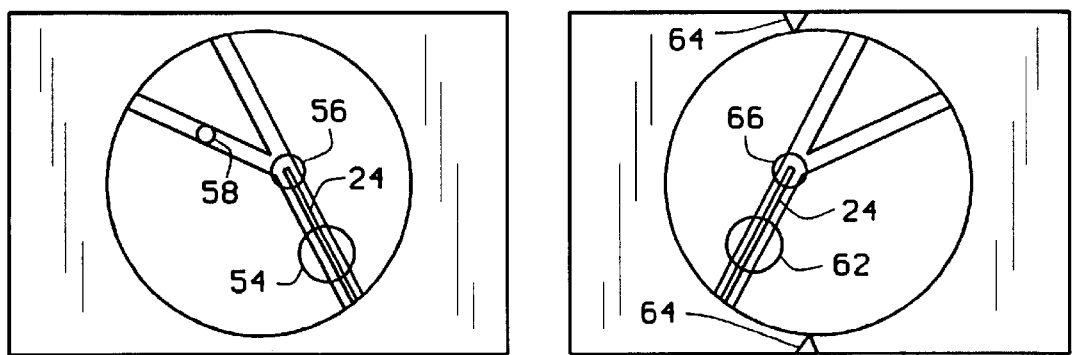
Figure 6F:
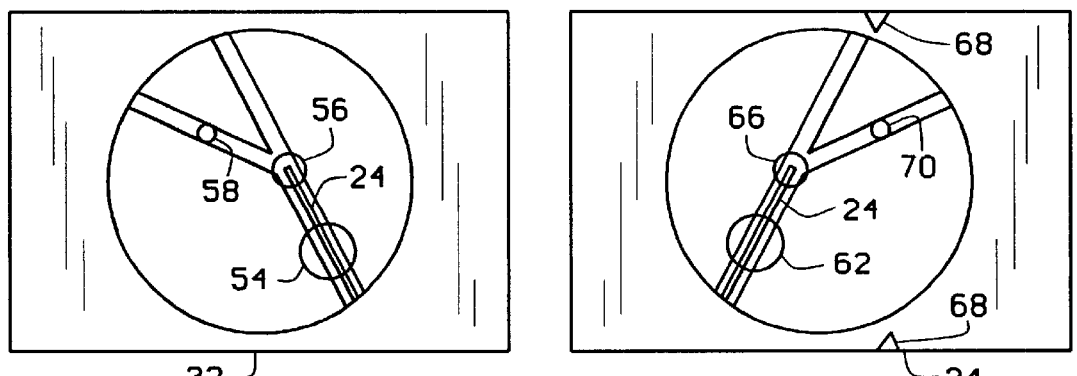
Figure 7:
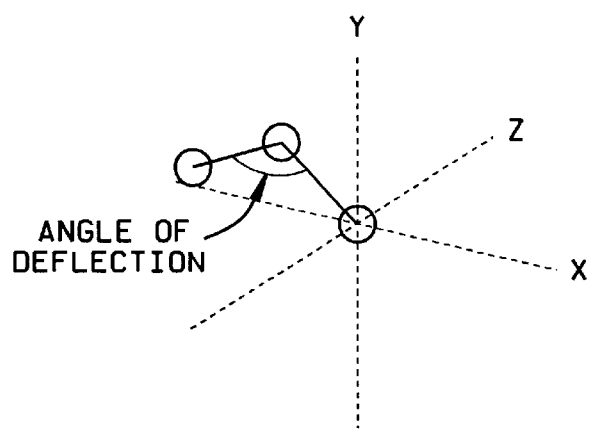
FIG. 7 is a perspective view illustrating the determination of the angle of deflection from the present catheter path to the desired catheter path in the second preferred embodiment.

The identification process in the three-point navigation system of the second preferred embodiment is shown in FIGS. 6A–6F. In FIG. 6A, the user uses joystick 38 on the joystick controller 36 to manipulate marker 54 on display 32 over a point on the current path of the catheter 24, and presses button 40 to lock the marker in place. As shown in FIG. 6B, a second marker 56 appears, and the user uses the joystick 38 to position this marker over the point where the user desires to change the direction of the catheter 24, and presses button 40 to lock the marker in position. As shown in FIG. 6C, a third marker 58 appears, and the user uses joystick 38 to position this marker over a point on the desired new path of the catheter 24, and presses button 40 to lock the marker in position. The user then switches to the second display 34. In the preferred embodiment this is done by using the joystick 38 to manipulate the cursor on the display to the side of the display 32 adjacent the display 34, which causes the cursor to switch to display 34. As shown in FIG. 6D, indicators 60 appear at the top and bottom of the display 34 to identify the line along which the marker 54 on display 32 lies, and the user uses the joystick 38 to manipulate marker 62 to the corresponding point on the display 34, and presses button 40 to lock the marker in position. As shown in FIG. 6E, indicators 64 appear at the top and the bottom of the display 34 to identify the line along which marker 56 on display 32 lies, and the user uses the joystick 38 to manipulate marker 66 to the corresponding point on display 34, and presses button 40 to lock the marker in position. As shown in FIG. 6F, indicators 68 appear at the top and the bottom of the display 34 to identify the line along which marker 58 on display 32 lies, and the user uses the joystick 38 to manipulate marker 70 to the corresponding point on display 34, and presses button 40 to lock the marker.

The markers 54 and 62, 56 and 66, and 58 and 70 each define a unique point in the three dimensional space in the body part. The computer 26 calculates the angle formed by these three points, which is the desired angle of deflection, and then controls the magnet system 22 to apply a magnetic field of sufficient direction and intensity to cause the distal tip of the catheter to bend at this angle. In the preferred embodiment the computer 26 controls the magnets to apply a magnetic field at a 90° over-torque, i.e., it leads the desired angle of deflection by 90°, in the same plane as the desired angle of deflection. This application of force normal to the desired orientation of the catheter 24 applies the maximum torque on the distal end of the catheter, and thus allows the minimum field intensity to be used. By applying a 90° over torque to the catheter tip, the magnetic field strength can be minimized while still achieving the desired angle of deflection. Reducing the magnetic field strength reduces the time it takes to apply the field. The strength of the applied magnetic field is preferably determined based on the properties (primarily the lag angle) of the catheter 24. In this second preferred embodiment, the intensity of the field required to achieve a desired angle of deflection with the application of a 90° over-torque is determined for a plurality of angles through experiment with a catheter of a given stiffness. For example the required field intensity is determined for the angles at 15° increments, i.e., for 15°, 30°, 45°, 60°, 75°, 90°, 105°, 120°, 135°, 150°, and 165°. Where the applied field is nearly axial, the bending of the distal end of the catheter 24 is unreliable. In such cases, the direction of the magnetic field is either limited to a predetermined maximum such as 170°, or the computer orients the catheter in two steps, first causing the magnet system 22 to apply a magnetic field of a first direction at a first intensity, and then causing the magnet system to apply a magnetic field of a second direction at a second intensity. The computer 26 uses the stored table of data and the desired angle of deflection to determine the intensity, interpolating for desired deflection angles that fall between the increments in the table.

The markers 54 and 62 on displays 32 and 34, respectively, identify a point on the current path of the catheter 24, and preferably have similar size and shape to indicate to the user that they identify the same point. In the second preferred embodiment markers 54 and 62 are large circles, but could, of course, have some other size, shape, and appearance. The markers 56 and 66 on displays 32 and 34, respectively, identify the point where the user desires to change the direction, and preferably have similar size and shape to indicate to the user that they identify the same point. In the second preferred embodiment markers 56 and 66 are medium circles, but could, of course, have some other size, shape, and appearance. Similarly, the markers 58 and 70 on screens 32 and 34, respectively, identify a point on the desired new path of the catheter, and preferably have similar sizes and shapes to indicate to the user that they identify the same point. In the second preferred embodiment markers 58 and 70 are small circles, but could, of course, have some other size, shape, and appearance.

The amount of time required to change the direction of the applied magnetic field is dependent on the field strength required to deflect the catheter 24 at a particular angle. Generally, the larger the deflection angle required, the stronger the magnetic field required. Thus, the magnitude of the field strength can be limited to a predetermined maximum, to minimize the delay during navigation, by preselecting a maximum catheter deflection angle. The user can select any deflection angle, but the actual angle would be limited to a preset maximum. While limiting the change to a predetermined maximum angle, the catheter can still be navigated successfully through the body, and the delay between magnetic field changes can be minimized. Thus, it is possible to preset the maximum angle of change, to for example 45° or some other suitable angle. In this example, all angles requested by the user would be reduced to 45°.

In the first preferred embodiment, the computer 26 is programmed to reconstruct the data for each of the points (the X-Z data input from display 32 and the Y-Z data input from display 34) into a point in three dimensional space. The computer 26 then determines the vector between the first point (identified by markers 42 and 48) and the second point (identified by markers 44 and 52), and controls the magnet system 22 to create a magnetic field within the body part in the same direction as the vector. Such a method of controlling the motion direction is disclosed in co-pending U.S. patent application Ser. No. 08-920,446, filed Aug. 29, 1997, entitled Method and Apparatus for Magnetically Controlling Motion Direction of a Mechanically Pushed Catheter. The strength of the magnetic field can be predetermined by the system or selected by the user, balancing the accuracy of the positioning of the catheter against the increased coil ramp time required for greater field strength.

In the second preferred embodiment, the computer 26 is programmed to reconstruct the data for each of the points (the X-Z data input from display 32 and the Y-Z data input from display 34) into a point in three dimensional space. The computer 26 then determines the vector between the first point (identified by markers 54 and 62) and the second point (identified by markers 56 and 66) and the vector between the second point and the third point (identified by markers 58 and 70), and the angle between these vectors, which equals the desired angle of deflection. The computer 26 adds 90° to the desired angle of deflection (in the same plane as the desired angle of deflection) to over torque the distal end of the catheter. The computer 26 automatically limits the angle of the magnetic field to less than a predetermined angle, preferably 170°. The computer 26 then determines the appropriate magnetic field intensity in a look-up table of empirically collected field intensities to achieve desired angle of deflections with a 90° over torque. The computer 26 linearly interpolates for angles of deflection between those in the look-up table.

The computer 26 then controls the magnet system 22 to establish a magnetic field in the body part with the determined field direction and field intensity.

The catheter is then manually advanced. Following advancement, the magnet system 22 is disabled to remove the external magnetic field. Alternatively, the physician could utilize the system to hold the catheter during treatment or pull the catheter.

Figure 2:
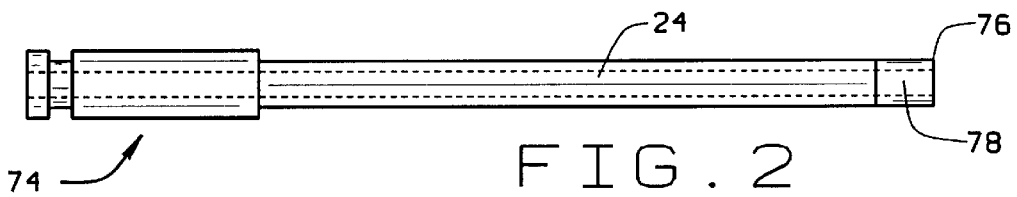
FIG. 2 is a top plan view of a magnet-tipped catheter of the type that can be used in the method and with the apparatus of this invention.
Figure 3:
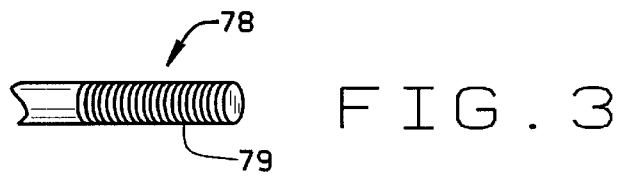
FIG. 3 is a perspective view of the distal end of the catheter, provided with a coil spring in accordance with an alternate construction of the present invention.

A catheter 24 adapted for use with the navigation method and apparatus of the present invention is shown in FIGS. 2 and 3. The catheter 24 has a proximal end 74 and a distal end 76. There is preferably at least one magnet 78 in the distal end of the catheter. This magnet 78 may either be a permanent magnet or a permeable magnet. The magnet 78 is of sufficient size to cause the distal end portion of the catheter to align with an applied magnetic field. The catheter 24 tends to resist this alignment because of stiffness of the material and other physical properties, and this resistance is manifested in a "lag angle" between the direction of the applied magnetic field at a given intensity, and the direction of the distal end of the catheter. In accordance with the principles of this invention, this lag angle is characterized, either as a formula or in a look-up table, so that it can be taken into account in determining the magnetic field intensity to apply to control the distal end of the catheter.

Figure 10:
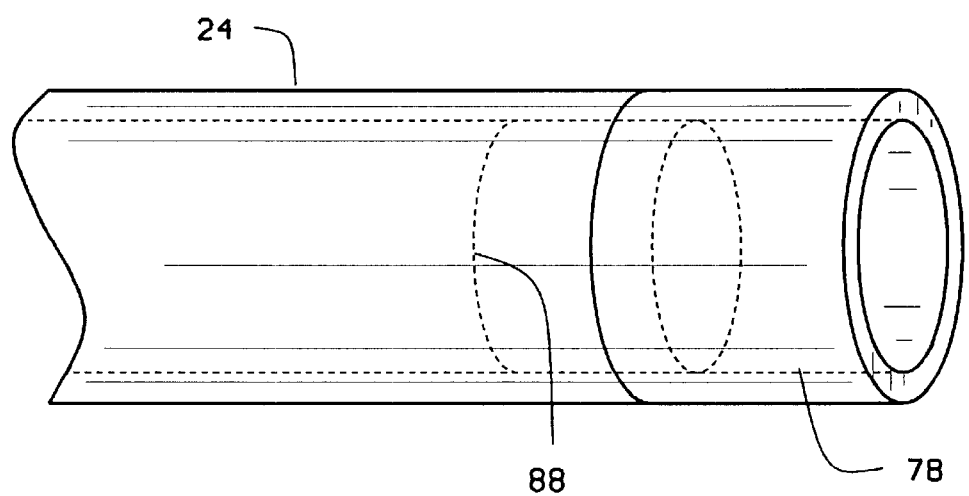
FIG. 10 is a perspective view of the distal end of a catheter showing a method of securing a magnet on the distal end.

The magnet 78 preferably has an annular shape and is secured at the distal end of the catheter, for example by embedding the magnet in the wall of the catheter, or attaching it to the end of the wall of the catheter, for example with adhesive. In an alternative construction, a plurality of spaced magnets can be provided in the distal end of the catheter. In the embodiment shown in FIG. 3, the magnet 78 is a coil 79 of magnetically permeable material embedded in the distal end portion of the wall of the catheter, which can be oriented in a magnetic field. In the embodiment shown in FIG. 10, a sleeve 88, which could be made from stainless steel or titanium, is disposed in the distal end of the catheter, and projects from the distal end, and an annular magnet 78 fits over the sleeve 88 and is secured, for example, with adhesive.

Figure 9:
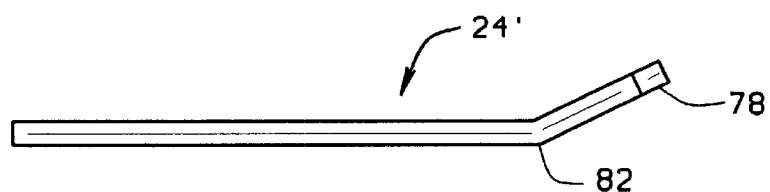
FIG. 9 is a perspective view of a catheter with a bent distal end portion according to an alternate construction of the present invention.

An alternative construction of the catheter 24' is shown in FIG. 9. Catheter 24' is similar in construction to catheter 24 except that the distal end portion of catheter 24' has a bend 82 formed therein. The catheter 24' works with the method and apparatus of the present invention. The application of a magnetic field causes the catheter 24' to rotate about its axis so that the bend faces the desired direction. The bend thus reduces the field strength that must be applied to orient the distal end of the catheter 24'. This reduces the amount of time required by the magnet system 22 and speeds navigation.

OPERATION

Figure 8:
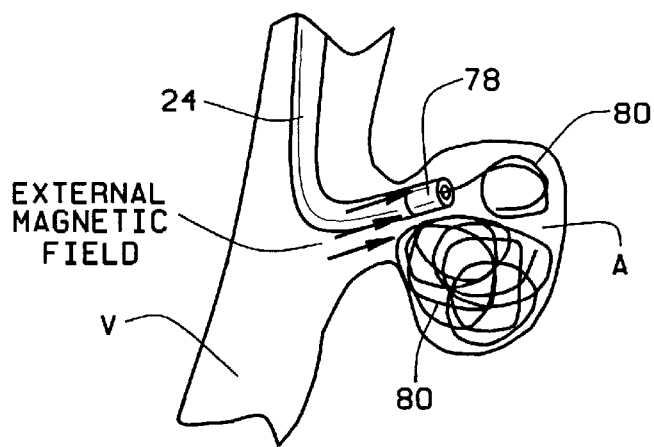
FIG. 8 is a schematic view of how the method and apparatus of the present invention can be used to guide and hold a catheter for the treatment of an aneurysm in a blood vessel.

An application of the navigation method and apparatus of the present invention is illustrated in FIG. 8, where, as part of an interventional neuroradiology procedure, platinum coils 80 are inserted into an aneurysm to occlude the aneurysm. In the past problems have occurred due to randomness in the placement of the coils. The location where a coil 80 ends up depends upon the position of the tip of the catheter 24. In FIG. 8, catheter 24 has been navigated through blood vessel V, to the site of an aneurysm A. The two-point or three-point navigation system for inputting the desired orientation of the end of the catheter 24 can be used to accurately orient the end of the catheter so that the catheter can be advanced into the aneurysm A, to deliver coils 80 or other therapeutic agents to the aneurysm A. The two-point or three point navigation of the present invention allows more precise control of the position of the distal end of the catheter 24, to better distribute the coils 80 in the aneurysm A.

What is claimed is:

1. A method of navigating a magnet-tipped distal end of an elongate medical device through the body, the method comprising the steps of:

providing bi-planar image displays of the body part through which the catheter is being navigated;

inputting points on a desired path for the medical device in three dimensions by identifying each point on the two bi-planar displays of the body part, including a first point on the current path of the medical device, a second point where the user desires to change the direction of the medical device, and a third point on the desired new path for the medical device;

determining the direction of a magnetic field capable of orienting the distal end of the medical device to correspond with the direction of the desired path between the second point and the third point, by determining the desired angle of deflection by determining the angle between a line between the first and second points and a line between the second and third points, and determining the direction of a magnetic field to achieve the desired angle of deflection and adding 90° to the desired angle of deflection;

applying the determined magnetic field to the distal end of the medical device to orient the distal end of the device in the direction of the desired path; and advancing the medical device to move the distal end of the device in the direction in which it is oriented by the magnetic field.

2. The method according to claim 1 wherein the maximum angle of the applied field is less than about 170°.

\* \* \* \* \*